United States Patent [19]
Kamihara et al.

[11] Patent Number: 5,849,945
[45] Date of Patent: Dec. 15, 1998

[54] AMINOTETRALONE DERIVATIVES AND PREPARATION PROCESS THEREOF

[75] Inventors: Shinji Kamihara; Kazuaki Kanai; Shigeru Noguchi, all of Tokyo, Japan

[73] Assignees: Daiichi Pharmaceutical Co., Ltd.; Kabushikikaisha Yakult Honsha, both of Tokyo, Japan

[21] Appl. No.: 894,230

[22] PCT Filed: Feb. 21, 1996

[86] PCT No.: PCT/JP96/00390

§ 371 Date: Aug. 21, 1997

§ 102(e) Date: Aug. 21, 1997

[87] PCT Pub. No.: WO96/26181

PCT Pub. Date: Aug. 29, 1996

[30] Foreign Application Priority Data

Feb. 22, 1995 [JP] Japan ................................ 7-033376

[51] Int. Cl.$^6$ ...................... C07C 233/15; C07C 233/41; C07C 231/12
[52] U.S. Cl. .............................. 560/28; 552/104; 560/25; 564/82; 564/92; 564/97; 564/99; 564/155; 564/158; 564/184; 564/202; 564/211; 564/222
[58] Field of Search ................................... 564/82, 92, 97, 564/99, 155, 158, 184, 211, 202, 222; 560/25, 28; 552/104

[56] References Cited

U.S. PATENT DOCUMENTS 5,637,770  6/1997  Terasawa et al. ...................... 564/211

FOREIGN PATENT DOCUMENTS 0495432A  7/1992  European Pat. Off. .

OTHER PUBLICATIONS

H. Neudeck & K. Schlögl: "Optisch aktive, aromatische Spirane, 8. Mitt." Monatshefte Für Chemie, vol. 110, No. 3, May/Jun. 1979, pp. 541–565, XP002052910 * p. 554, line 15–line 25; example 1A *.

Primary Examiner—Richard L. Raymond
Attorney, Agent, or Firm—Oblon, Spivak, McClelland, Maier & Neustadt, P.C.

[57] ABSTRACT

The present invention pertains to a process for the preparation of Compound (4) through the below-described reaction route:

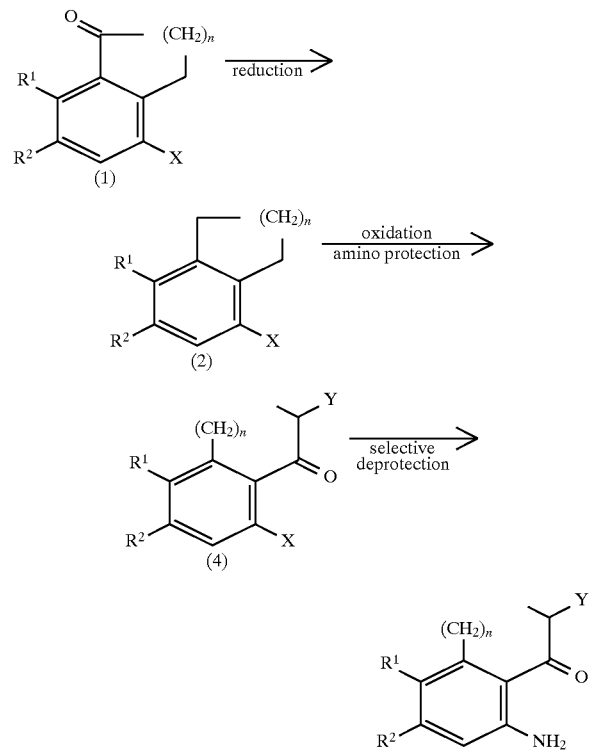

wherein $R^1$ and $R^2$ each represents H, halogen, OH or $C_{1-6}$ alkyl group; X and Y each represents a protected amino group and n stands for 0 to 4. According to the above process, an aminotetralone derivative which is an intermediate useful for an industrial preparation of a camptothecin derivative can be obtained in a convenient manner and in a high yield.

4 Claims, No Drawings

AMINOTETRALONE DERIVATIVES AND PREPARATION PROCESS THEREOF

This application is a 371 of PCT/JP96/00390, field Feb. 21, 1996.

TECHNICAL FIELD

This invention relates to an aminotetralone derivative which is an intermediate for the preparation of a camptothecin derivative (refer to Japanese Patent Application Laid-Open No. 87746/1994), an antitumor agent; and a preparation process thereof.

BACKGROUND ART (1S, 9S)-1-Amino-9-ethyl-5-fluoro-2,3-dihydro-9-hydroxy-4-methyl-1H, 12H-benzo[de]pyrano[3', 4':6,7]-indolizino[1,2-b]quinoline-10,13(9H, 15H)-dione represented by the following formula (6):

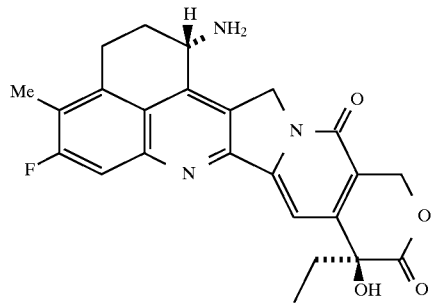

is a camptothecin derivative which exhibits excellent antitumor activities.

Such a camptothecin derivative can be prepared, for example, by the synthesis route, which will be described below, through the reaction between 8-amino-6-fluoro-5-methyl-2-(protected amino)-1-tetralone and (4S)-4-ethyl-7,8-dihydro-4-hydroxy-1H-pyrano[3,4-f]indolizine-3,6,10(4H)-trione (refer to Japanese Patent Application Laid-Open No. 87746/1994).

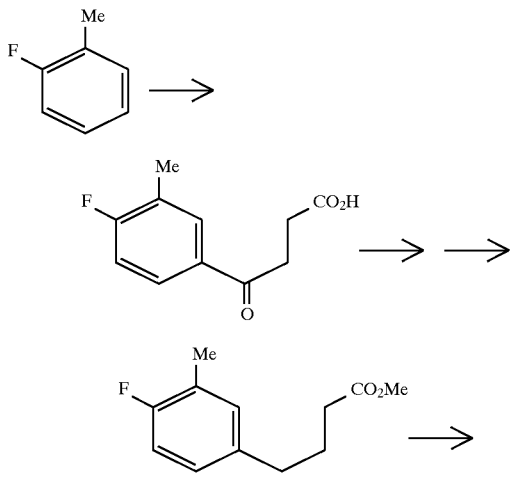

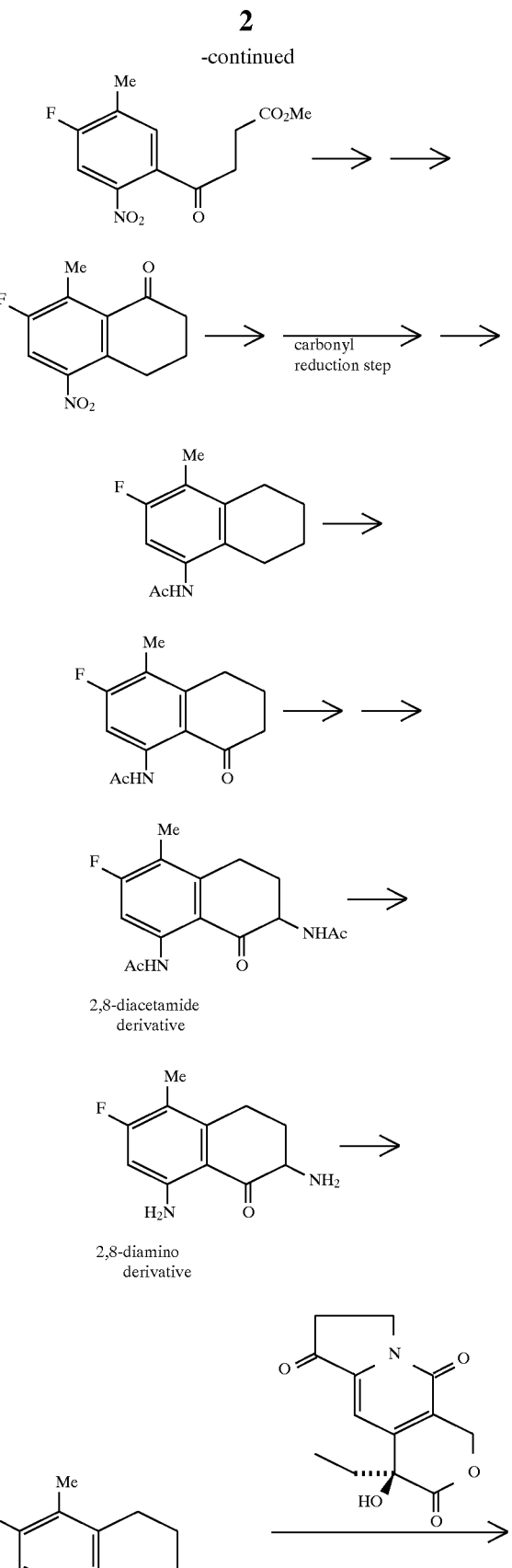

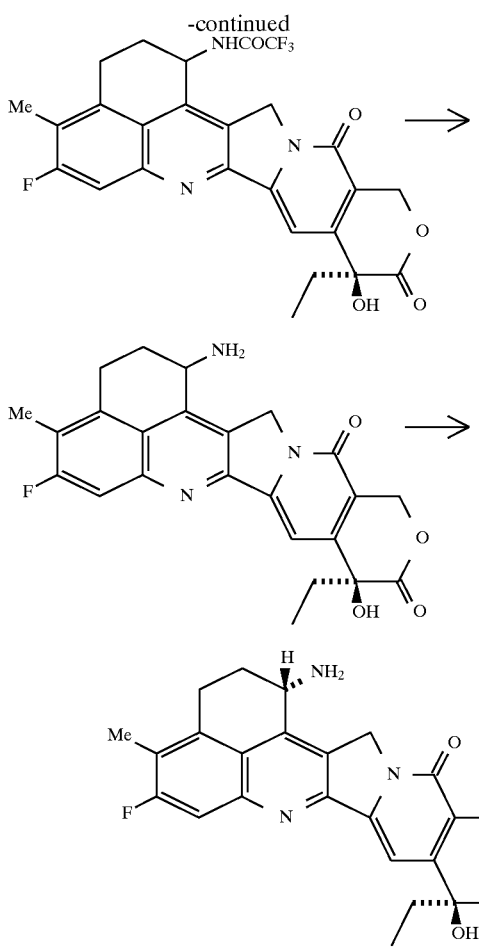

The previous process for the preparation of 8-amino-6-fluoro-5-methyl-2-amino-1-tetralone which is a synthesis intermediate useful for the preparation of a camptothecin derivative is however accompanied with the drawbacks that in the first place, a multi-stage step including alcohol formation, dehydration and reduction of a double bond is necessary for the reduction of a carbonyl group; and in the second place, although an amino group at the 2-position is selectively protected after a 2,8-diacetamide derivative is once converted into a 2,8-diamino derivative, the resulting 2,8-diamino derivative is unstable, resulting in a low yield of the target product (refer to Japanese Patent Application Laid-Open No. 87746/1994). There is accordingly a demand for the development of an industrially excellent preparation process.

An object of the present invention is therefore to provide a process for the preparation of an 8-amino-2-(protected amino)-1-tetralone derivative, which is a synthesis intermediate useful for the industrial preparation of a camptothecin derivative, in a convenient manner and in a high yield.

DISCLOSURE OF THE INVENTION

With the foregoing in view, the present inventors have conducted an extensive investigation. As a result, it has been found that the reduction of a carbonyl group can be conducted efficiently by using a palladium catalyst and an 8-amino-2-(protected amino)-1-tetralone derivative can be obtained by a short step and in a high yield with-out isolating an unstable 2,8-diamino derivative by subjecting a 2,8-di(protected amino) derivative to a treatment with an acid to selectively eliminate the protective group from the 8-(protected amino) group, leading to the completion of the present invention.

The preparation process of the 8-amino-2-(protected amino)-1-tetralone derivative (5) according to the present invention can be represented by the following reaction scheme:

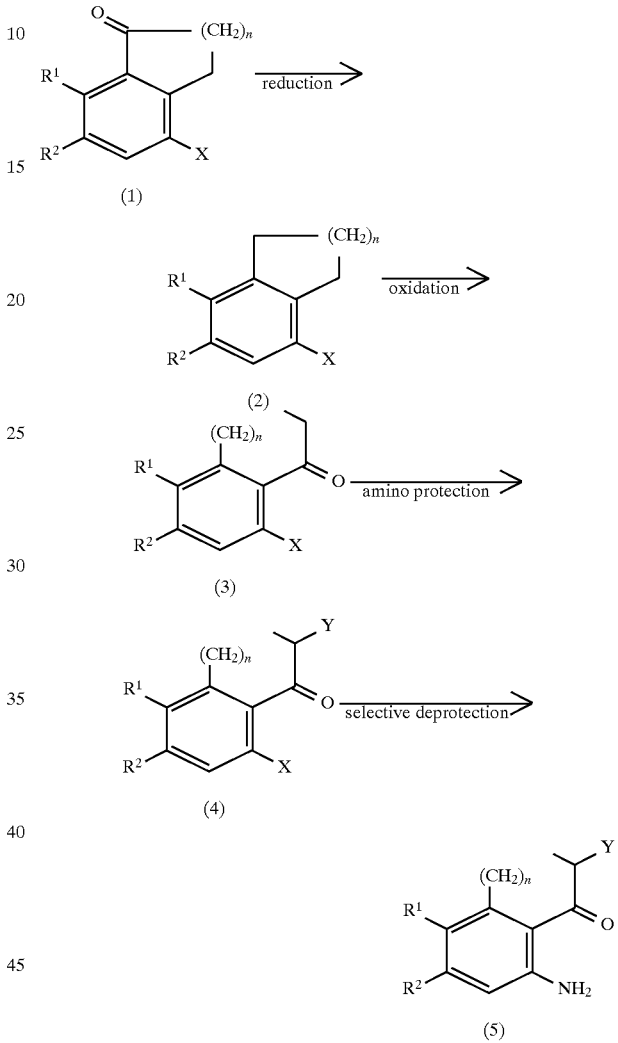

wherein $R^1$ and $R^2$ each independently represents a hydrogen atom, a halogen atom, a hydroxyl group or a $C_{1-6}$ alkyl group, X and Y each independently represents an amino group having a protective group and n stands for an integer of 0 to 4.

Described specifically, Compound (5) is prepared by hydrogenating Compound (1) into Compound (2) in the presence of a palladium catalyst, oxidizing the resulting Compound (2) into Compound (3), protecting the amino group of the resulting Compound (3) to obtain Compound (4), and reacting the resulting Compound (4) with an acid to eliminate only the protective group of the amino group at the 8-position. Among the above-described steps, the steps to obtain Compound (4) from Compound (2) are described in Japanese Patent Application Laid-Open No. 87746/1994 or the like. Accordingly, the present invention provides the steps for the preparation of Compound (2) from Compound (1) and Compound (5) from Compound (4).

BEST MODES FOR CARRYING OUT THE INVENTION

In the above reaction scheme, preferred examples of $R^1$ and $R^2$ include a methyl group, ethyl group, n-propyl group, isopropyl group, fluorine atom, chlorine atom and bromine atom. Particularly preferred is the case where $R^1$ and $R^2$ represent a methyl group and a fluorine atom, respectively. As n, 2 is particularly preferred.

Examples of the protective group for the protected amino group represented by X or Y include alkoxycarbonyl groups such as tertiary butoxycarbonyl and 2,2,2-trichloroethoxycarbonyl; aralkyloxycarbonyl groups such as benzyloxycarbonyl, paramethoxybenzyloxycarbonyl and paranitrobenzyloxycarbonyl; acyl groups such as acetyl, methoxyacetyl, trifluoroacetyl, chloroacetyl, pivaloyl, formyl and benzoyl; alkyl or aralkyl groups such as tertiary butyl, benzyl, paranitrobenzyl, paramethoxybenzyl and triphenylmethyl; alkylsulfonyl or halogenoalkylsulfonyl groups such as methanesulfonyl and trifluoromethanesulfonyl; and arylsulfonyl groups such as benzenesulfonyl and toluenesulfonyl. Among them, an acyl group, particularly alkanoyl or benzoyl group which may be substituted by a halogen atom is preferred.

A specific description will next be made of with reference to the above reaction scheme.

A starting Compound (1) can be prepared, for example, according to the following reaction scheme:

the amino group, and then carrying out ring closure. Incidentally, Compound (10) can also be obtained by reacting Compound (7) with y-butyrolactone in the presence of an acid catalyst.

Compound (2) can be obtained by hydrogenating Compound (1) in the presence of a palladium catalyst. This reaction can be effected either under acidic or neutral conditions.

In the case of the hydrogenation reaction under acidic conditions, it may be effected by dissolving Compound (1) in a solvent, mixing the resulting solution with a solution of activated carbon and palladium chloride dissolved in an acid and then, stirring the resulting mixture under a hydrogen gas atmosphere.

No particular limitation is imposed on the solvent insofar as it is inert to the hydrogenation reaction. Those miscible with water are preferred. Specific examples include alcohols such as methanol, ethanol and isopropyl alcohol; ethers such as dioxane and tetrahydrofuran; and acetic acid and ethyl acetate.

The solvent is used in an amount ranging from 5 times to 100 times relative to Compound (1) [volume/weight; the ratio will be designated as 1 times when the solvent is used in an amount of 1 ml relative to 1 g of Compound (1)], with 10 to 30 times being preferred.

An inorganic acid may be used as the acid for the preparation of the palladium chloride solution. Ordinarily, hydrochloric acid or sulfuric acid can be used. The concentration of such an acid is 5 wt.% or higher, with 15 to 25

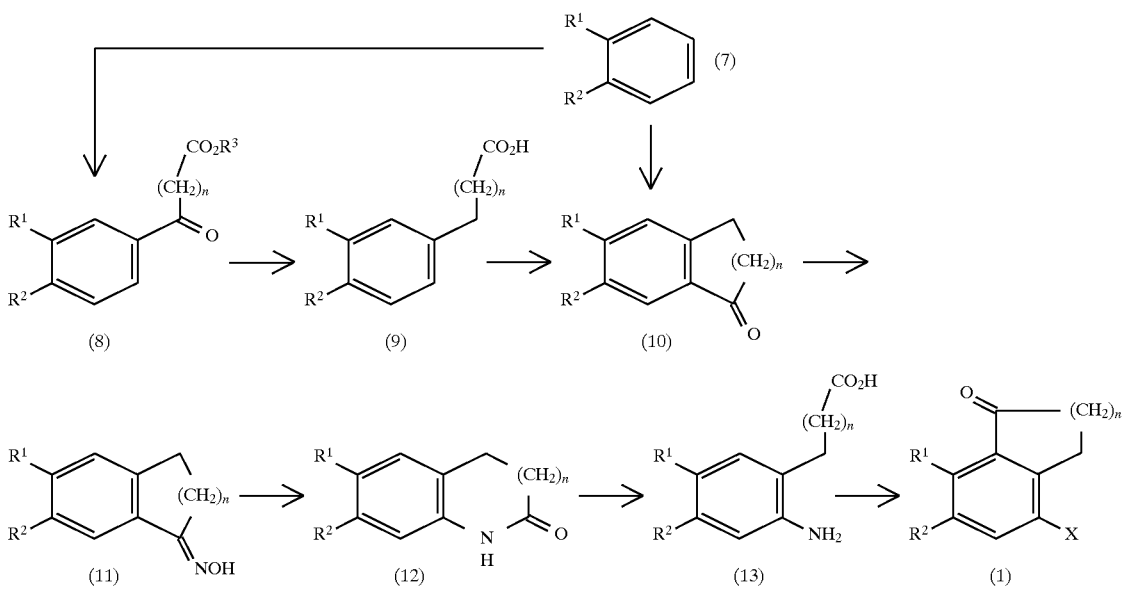

wherein $R^3$ represents a hydrogen atom or carboxyl-protective group and $R^1$, $R^2$, n and X have the same meanings as defined above.

Described specifically, Compound (1) can be obtained by reacting Compound (7) with a dicarboxylic anhydride such as succinic anhydride in the presence of a Lewis acid to obtain Compound (8), hydrogenating the resulting Compound (8) into Compound (9) in the presence of a palladium catalyst, cyclizing the resulting Compound (9) into Compound (10) in the presence of an acid, reacting the resulting Compound (10) with hydroxylamine to obtain Compound (11), converting the resulting Compound (11) into Compound (12) by Beckmann rearrangement, ring-opening the resulting Compound (12) into Compound (13), protecting wt.% being more preferred. The acid is employed in an amount of 3 to 10 times, preferably about 5 times the weight of palladium chloride.

Palladium chloride may be used in an amount of 0.01 to 0.1 equivalent (mole) relative to Compound (1), with about 0.03 equivalent being preferred.

As the activated carbon, those commercially available as activated charcoal can be used. The activated carbon may be used in an amount of about 3 to 10 times, preferably 5 times the weight of palladium chloride.

The pressure of the hydrogen gas may be atmospheric pressure. Alternatively, the reaction can be reacted under pressure.

The hydrogenation can be conducted by stirring at room temperature to about 50° C., preferably room temperature, for one hour to several days, preferably about 5 hours.

In the case of the hydrogenation reaction under neural conditions, a method using a palladium-carbon catalyst can be given as an example. Described specifically, the hydrogenation may be carried out by dissolving Compound (1) in a solvent, and then stirring a mixture of the resulting solution and the palladium-carbon catalyst under a pressurized hydrogen gas atmosphere.

No particular limitation is imposed on the solvent insofar as it is inert to the hydrogenation reaction. Specific examples include alcohols such as methanol, ethanol and isopropyl alcohol; ethers such as dioxane and tetrahydrofuran; and acetic acid and acetate esters such as ethyl acetate.

The solvent may be used in a similar amount to the above method in which palladium chloride is used.

As the palladium-carbon catalyst, that borne on a carbon may be used. Its palladium content is preferably 5 to 10% and about 0.2 equivalent (molar) relative to Compound (1) is preferred.

The hydrogenation reaction may be effected in a hermetically-sealed vessel such as autoclave. It is preferred to effect the reaction under hydrogen gas atmosphere of 10 to 100, particularly about 40 atmospheric pressure, at room temperature to 100° C., particularly about 50° C., for one hour to several days.

Compound (4) can be obtained by oxidizing Compound (2) with potassium permanganate or the like, followed by amination and then acetylation, which may be effected in a manner known to date (the process described in Japanese Patent Application Laid-Open No. 87746/1994 or the like process).

Compound (5) may be obtained by a treatment of Compound (4) with an acid. Examples of the acid include inorganic acids such as diluted hydrochloric acid, diluted sulfuric acid and hydrobromic acid; and organic acids such as acetic acid, trifluoroacetic acid and methanesulfonic acid.

The acid is preferably used in an amount of about 10 times (volume/weight) relative to Compound (4). It is also possible to allow the above-exemplified acid to serve as a solvent.

A solvent inert to the acid treatment of Compound (4) can also be employed. Examples of the inert solvent include alcohols, dioxane and tetrahydrofuran. It is preferred to carry out the treatment with an acid at room temperature to 100° C., more preferably 60° C., for 1 to 24 hours, particularly about 2 hours.

EXAMPLES

The present invention will hereinafter be described in further detail by Examples. It should however be borne in mind that they are merely illustrative and are not intend to limit the present invention thereto.

Referential Example 1

Preparation process of 4-(4-fluoro-3-methylphenyl)-4-oxobutanoic acid

In a mixed solution of 2.0 g of succinic anhydride and 50 ml of 1,2-dichloroethane, 6.7 g of aluminum chloride were added, followed by stirring at room temperature for 40 minutes. To the resulting mixture, 20 ml of 2-fluorotoluene were added dropwise at room temperature and they were stirred for 20 minutes, followed by further stirring for 20 minutes at an external temperature of 50° C. The reaction mixture was cooled and then poured into ice water to which 5% hydrochloric acid had been added. The resulting mixture was extracted with chloroform. The chloroform layer was washed with water and dried over anhydrous magnesium sulfate. The solvent was then evaporated. The residue so obtained was recrystallized from chloroform, whereby 3.2 g of the title compound was obtained.

Referential Example 2

Preparation process of 4-(4-fluoro-3-methylphenyl) butanoic acid

In methanol, 10.0 g of 4-(4-fluoro-3-methylphenyl)-4-oxobutanoic acid were dissolved, followed by the addition of 1.5 g of activated charcoal (Norit EXW) and 12.4 ml of a palladium chloride solution (a solution obtained by dissolving 2.2 ml of concentrated hydrochloric acid and 2.5 ml of water to 1.0 g of palladium chloride with heating to give a total volume of 50 ml). The resulting mixture was subjected to catalytic reduction at room temperature and atmospheric pressure for 6 hours. After the completion of the reaction, the catalyst was filtered out by a glass filter paper, followed by washing with 12 ml of methanol. To the filtrate, 100 ml of a 5% aqueous solution of sodium hydroxide were added and the mixture was stirred for one hour. After the completion of the reaction, methanol was evaporated and the residue was adjusted to acidic with 12 ml of concentrated hydrochloric acid under ice cooling. The crystals so precipitated were collected by filtration, whereby 8.8 g of the title compound was obtained.

Referential Example 3

Preparation process of 4-(4-fluoro-3-methylphenyl) butanoic acid

In a 50-ml autoclave, 1.0 g of 4-(4-fluoro-3-methylphenyl)-4-oxobutanoic acid and 2.5 ml of methanol were charged, followed by the addition of 0.1 g of 10% palladium-carbon. After hydrogen pressure was increased to 30 kg/cm$^2$ at room temperature, the resulting mixture was stirred at 50° C. for 3.5 hours. After the completion of the reaction, the reaction mixture was filtered, followed by washing with methanol. The filtrate was thereafter concentrated under reduced pressure. Water was added to the residue so obtained. The crystals so precipitated were filtered, washed with water and dried under reduced pressure, whereby 0.82 g of the title compound was obtained.

Referential Example 4

Preparation process of 7-fluoro-6-methyl-1-tetralone (Process 1)

To a mixed solution of 1.5 ml of 2-fluorotoluene and 0.5 ml of γ-butyrolactone, 1.3 g of aluminum chloride were added at room temperature, followed by stirring at the same temperature for 20 hours. After the completion of the reaction, the reaction mixture was poured to a 5% aqueous solution of hydrochloric acid. The resulting solution was extracted with chloroform. The chloroform layer was washed with water and dried over anhydrous magnesium sulfate. The solvent was removed under reduced pressure. To the residue, 5 ml of concentrated sulfuric acid were added under ice cooling, followed by stirring for one hour. After the completion of the reaction, the reaction mixture was poured into water, followed by extraction with chloroform. The chloroform layer was washed with water and then dried over anhydrous magnesium sulfate. The solvent was removed under reduced pressure, whereby 1 g of the residue was obtained. The residue so obtained ws found to be a 1:1 mixture of the title compound and its isomer as a result of $^1$H-NMR spectrum.

(Process 2)

To 150 ml of concentrated sulfuric acid, 20.0 g of 4-(4-fluoro-3-methylphenyl)-butanoic acid were added in portions over 40 minutes under ice cooling and the mixture was stirred for one hour under the same conditions. After the completion of the reaction, the reaction mixture was poured into ice water. The crystals so precipitated were collected by filtration, followed by sufficient washing. The product so obtained was provided for use in the subsequent step in the wet form.

$^1$H-NMR (CDCl$_3$)δ: 2.07–2.15(2 H,m), 2.30(3 H,d,J=2.0 Hz), 2.62(2 H,t,J=6.4 Hz), 2.88(2 H,t,J=6.1 Hz), 7.08(1 H,d,J=7.6 Hz), 7.63(1 H,d,J=7.9 Hz).

Referential Example 5

Preparation process of 7-fluoro-methyl-1-tetralone oxime

To a solution of 10.6 g of hydroxyammonium chloride and 12.6 g of sodium acetate in water (50 ml), the whole amount of 7-fluoro-6-methyl-1-tetralone obtained in Process 2 of Example 4 was added, to which 300 ml of ethanol were added. The resulting mixture was stirred for 3 hours at an external temperature of 70° to 75° C. After the completion of the reaction, the solvent was removed under reduced pressure. Water was added to the residue and crystals so precipitated were collected by filtration. After washing with water, the crystals were dried under reduced pressure, whereby 15.3 g of the title compound was obtained.

$^1$H-NMR (CDCl$_3$)δ: 1.80–1.90(2 H,m), 2.25(3 H,d,J=1.7 Hz), 2.69(2 H,t,J=6.1 Hz), 2.78(2 H,t,J=6.6 Hz), 6.96(1 H,d,J=7.6 Hz), 7.50(1 H,d,J=10.9 Hz).

Referential Example 6

Preparation process of 3,4-dihydro-8-fluoro-7-methyl-2-oxo-1-benzazepine

To 70 ml of 85% phosphoric acid, 100 g of phosphoric anhydride were added in portions. After the phosphoric anhydride was dissolved thoroughly, 10.0 g of 7-fluoro-6-methyl-1-tetralone oxime were added to the resulting solution over 20 minutes at an external temperature of 90° C., followed by stirring for 4 hours under the same conditions. After the completion of the reaction, the reaction mixture was poured into ice water. The crystals so precipitated were collected by filtration. The crystals so obtained were recrystallized from chloroform-diethyl ether, whereby 8.3 g of the title compound was obtained.

$^1$H-NMR (CDCl$_3$)δ: 2.15–2.23(2 H,m), 2.24(3 H,d,J=1.5 Hz), 2.35(2 H,t,J=3 Hz), 2.73(2 H,t,J=7.1 Hz), 6.71(1 H,d,J=9.9 Hz), 7.01(1 H,d,J=8.3 Hz), 8.45(1 H,br-s).

Referential Example 7

Preparation process of (4-(2-acetylamino-4-fluoro-5-methylphenyl)butanoic acid

To 1.0 g of 3,4-dihydro-8-fluoro-7-methyl-2-oxo-1-benzazepine, 15 ml of methanol and 0.7 ml of concentrated hydrochloric acid were added and they were heated under reflux for 3 hours. After the completion of the reaction, the reaction mixture was allowed to cool and the solvent was removed under reduced pressure. To the white residue so obtained, 20 ml of methylene chloride were added, followed by the addition of 1.8 ml of triethylamine and then 0.5 ml of acetic anhydride under ice cooling. They were stirred at room temperature for 2.5 hours. After the completion of the reaction, water and a 5% aqueous hydrochloric acid solution were added to the reaction mixture, followed by extraction with chloroform. The chloroform layer was washed with a saturated aqueous solution of sodium bicarbonate and then dried over anhydrous magnesium sulfate. The solvent was then evaporated. To the residue so obtained, 8 ml of methanol and 5 ml of a 5% aqueous solution of sodium hydroxide were added and the mixture was stirred at room temperature for 30 minutes. The solvent was then distilled off under reduced pressure. To the residue so obtained, a 5% aqueous hydrochloric acid solution was added, followed by extraction with ethyl acetate. The ethyl acetate layer was washed with saturated saline and then dried over anhydrous magnesium sulfate. The solvent was then evaporated. The residue so obtained was recrystallized from ethyl acetate-chloroform, whereby 0.8 g of the title compound was obtained.

$^1$H-NMR (CDCl$_3$)δ: 1.71–1.85(2 H,m), 2.20(3 H,d,J=1.5 Hz), 2.20(3 H,s), 2.47–2.59(4 H,m), 6.91(1 H,d,J=8.6 Hz), 7.92(1 H,d,J=12.2 Hz), 8.43(1 H,br-s).

Referential Example 8

Preparation Process of 5-acetylamino-7-fluoro-8-methyl-l-tetralone

In 50 ml of methylene chloride, 5.0 g of 4-(2-acetylamino-4-fluoro-5-methylphenyl)butanoic acid was suspended. To the suspension, 4.3 ml of thionyl chloride was added dropwise over 2 minutes at an internal temperature of 3° to 4° C., followed by stirring at the same temperature for 15 minutes and then at room temperature for 45 minutes. To the resulting mixture, 6.6 g of aluminum chloride were added over 5 minutes at an internal temperature of 4° to 6° C., followed by stirring for one hour at the same temperature and then stirring for 24 hours at room temperature. After the completion of the reaction, a 5% aqueous hydrochloric acid solution and ice were added gradually to the reaction mixture and they were stirred for a while. The reaction mixture was extracted with chloroform. The chloroform layer was washed sufficiently with water and a saturated aqueous solution of sodium bicarbonate, and was then dried over potassium carbonate. The solvent was removed under reduced pressure. To the residue so obtained, isopropyl ether was added. The crystals so precipitated were collected by filtration, whereby 3.5 g of the title compound was obtained.

$^1$H-NMR (CDCl$_3$)δ: 2.05–2.14(2 H,m), 2.22(3 H,s), 2.50(3 H,d,J=2.3 Hz), 2.64(2 H,t,J=6.6 Hz), 2.77(2 H,t,J=6.4 Hz), 7.07(1 H,br-s), 7.64(1 H,d,J=10.8 Hz).

Example 1

Preparation process of 5-acetylamino-7-fluoro-8-methyl-1,2,3,4-tetrahydronaphthalene To 20.0 g of 5-acetylamino-7-fluoro-8-methyl-1-tetralone, 1000 ml of methanol, 7.2 g of activated charcoal (Norit EXW) and 60 ml of a palladium chloride solution (a 100 ml solution obtained by adding 4.5 ml of concentrated hydrochloric acid and 4.5 ml of water to 2.0 g of palladium chloride and dissolving them with heating) were added. The resulting mixture was subjected to catalytic reduction at room temperature and atmospheric pressure for 8 hours.

After the completion of the reaction, the catalyst was filtered off by a glass filter paper and then washed thoroughly with chloroform-methanol. The filtrate was then concentrated to dryness under reduced pressure. The residue so obtained was recrystallized from chloroform-methanol, whereby 14.4 g of the title compound was obtained.

Example 2

Preparation process of 5-acetylamino-7-fluoro-8-methyl-1,2,3,4-tetrahydronaphthalene In a 50-ml autoclave, 1.0 g of 5-acetylamino-7-fluoro-8-methyl-l-tetralone and 10 ml of methanol were charged. To the resulting mixture, 0.5 g of 10% palladium-carbon was added. The hydrogen pressure was increased to 40 kg/cm$^2$ at room temperature, under which the resulting mixture was stirred at 50° C. for 18 hours. After the completion of the reaction, the reaction mixture was filtered. The catalyst so obtained was washed with chloroform and then the filtrate was concentrated under reduced pressure. To the residue, isopropyl ether was added. The crystals so precipitated were collected by filtration, followed by drying under reduced pressure, whereby 0.76 g of the title compound was obtained.

Referential Example 9

Preparation process of 8-acetylamino-6-fluoro-5-methyl-1-tetralone

In acetone, 5.0 g of 5-acetylamino-7-fluoro-8-methyl-1,2,3,4-tetrahydronaphthalene were suspended, followed by the addition of 2.3 g of sodium bicarbonate. To the resulting mixture, 13.9 g of potassium permanganate were added in portions over 3.5 hours at an internal temperature of 10° to 15° C. and the mixture was stirred at room temperature for one hour. To the resulting mixture, 0.8 g of potassium permanganate was added further, followed by stirring for 1.5 hours. After a 5% aqueous solution of sodium hydrogensulfite was added in a small amount and the complete disappearance of potassium permanganate was confirmed, manganese dioxide so precipitated was filtered out. The manganese dioxide was washed thoroughly with chloroform and the filtrate was removed under reduced pressure. The residue so obtained was dissolved in chloroform. The resulting solution was washed three times with a saturated aqueous solution of sodium bicarbonate and dried over potassium carbonate. The solvent was evaporated under reduced pressure. The residue so obtained was recrystallized from chloroform-diethyl ether, whereby 2.6 g of the title compound was obtained.

Referential Example 10

Preparation process of 2,8-diacetylamino-6-fluoro-5-methyl-1-tetralone

In 550 ml of tetrahydrofuran, 19.1 g of potassium tertiary butoxide were suspended. To the resulting suspension, a solution, which had been obtained by dissolving 20.0 g of 8-acetylamino-6-fluoro-5-methyl-1-tetralone in 250 ml of tetrahydrofuran at an internal temperature of 4° to 5° C. under a nitrogen gas stream, was added dropwise over 35 minutes and the mixture was stirred at the same temperature for 10 minutes. To the resulting mixture, 20 ml of n-butyl nitrite were added at an internal temperature of 5° to 7° C. over 15 minutes, followed by stirring at the same temperature for one hour. After the completion of the reaction, water was added to the reaction mixture. The resulting aqueous solution was adjusted to pH 3 to 4 with a 5% aqueous solution of hydrochloric acid, followed by filtration through a glass filter paper. The filtrate was evaporated under reduced pressure and the crystals so precipitated were collected by filtration. The crystals so collected were washed with water, dried and then dissolved in a mixed solution of 200 ml of acetic anhydride and 200 ml of acetic acid. Under ice cooling, 25 g of zinc powder was added to the resulting solution at an internal temperature of 6° to 15° C. over 1.5 hours. The resulting mixture was stirred at the same temperature for 30 minutes and then, the solid matters were filtered out. The solid matters so obtained were washed successively with chloroform and ethyl acetate. The filtrate was then concentrated under reduced pressure. Water was added to the residue so obtained and then substantially neutralized with a 5% aqueous solution of sodium hydroxide. The crystals so precipitated were stirred for a while under the condition of a slurry, followed by collection through filtration. The crystals so collected were washed with water and dried under reduced pressure, whereby 16.5 g of the title compound was obtained.

Example 3

Preparation process of 2-acetylamino-8-amino-6-fluoro-5-methyl-1-tetralone

To 8.0 g of 2,8-diacetylamino-6-fluoro-5-methyl-1-tetralone, 120 ml of a 20% aqueous solution of hydrochloric acid were added and the mixture was stirred at an external temperature of 60° C. for 2 hours. After the completion of the reaction, the reaction mixture was cooled and was added with 100 ml of water. The resulting mixture was filtered through a Kiriyama funnel. To the filtrate, further 100 ml of water were added, followed by extraction with chloroform. To the chloroform layer so obtained, potassium carbonate and Florisil were added and they were stirred for a while. The resulting mixture was filtered and then, the solvent was removed under reduced pressure. The residue so obtained was recrystallized from chloroform-diethyl ether, whereby 3.4 g of the title compound was obtained.

Melting point: 212° to 214° C.

$^1$H-NMR (CDCl$_3$)δ: 1.66–1.85(1 H,m), 2.05(3 H,d,J=1.3 Hz), 2.09(3 H,s), 2.70–2.80(1 H,m), 2.89–2.96(2 H,m), 4.49(1 H,ddd,J=5.0,5.0,13.5 Hz), 6.22(1 H,d,J=11.6 Hz), 6.33(2 H,br-s), 6.64(1 H,br-s).

CAPABILITY OF EXPLOITATION IN INDUSTRY

An aminotetralone derivative which is a synthesis intermediate useful for the industrial preparation process of a camptothecin derivative can be obtained in a convenient manner and in a high yield.

We claim:

1. A process for the preparation of a compound represented by the following formula (2):

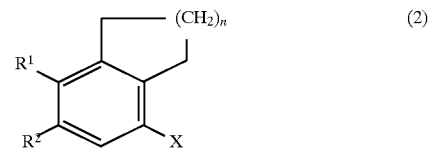

wherein R$^1$ and R$^2$ each independently represents a hydrogen atom, a halogen atom, a hydroxyl group or a $C_{1-6}$ alkyl group, X represents an amino group having a protective group and n stands for an integer of 0 to 4, which comprises, in the presence of a palladium catalyst, hydrogenating a compound represented by the following formula (1):

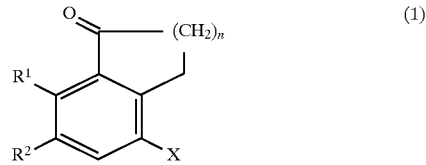

wherein X, $R^1$, $R^2$ and n have the same meanings as defined above.

2. A process according to claim 1, wherein $R^1$ represents a methyl group, $R^2$ represents a fluorine atom, X represents an acetylamino group and n stands for 2.

3. A process according to claim 1, wherein the hydrogenating is effected under acid conditions by dissolving Compound (1) in a solvent, mixing the resulting solution with a solution of activated carbon and palladium chloride dissolved in an acid, and stirring the resulting mixture under a hydrogen gas atmosphere.

4. A process according to claim 1, wherein the hydrogenating is effected under neutral conditions by dissolving Compound (1) in a solvent, mixing the resulting solution with a palladium-carbon catalyst and stirring the resulting mixture under a pressurized hydrogen gas atmosphere.

* * * * *